United States Patent [19]
Hoenk

[11] Patent Number: 5,739,416
[45] Date of Patent: Apr. 14, 1998

[54] FAST, HIGH SENSITIVITY DEWPOINT HYGROMETER

[75] Inventor: Michael E. Hoenk, Valencia, Calif.

[73] Assignee: California Institute of Technology, Pasadena, Calif.

[21] Appl. No.: 715,417

[22] Filed: Sep. 18, 1996

[51] Int. Cl.⁶ .......................... G01N 25/68; G01W 1/00
[52] U.S. Cl. .................. 73/29.01; 73/29.04; 73/597; 324/664; 374/28
[58] Field of Search .................. 73/29.01, 29.02, 73/24.04, 597; 374/28; 324/664

[56] References Cited

U.S. PATENT DOCUMENTS

| | | | |
|---|---|---|---|
| 4,163,384 | 8/1979 | Blakemore | 73/29 |
| 4,312,228 | 1/1982 | Wohltjen | 73/597 |
| 4,378,168 | 3/1983 | Kuisma et al. | 374/28 |
| 4,768,378 | 9/1988 | Ando et al. | 73/336.5 |
| 4,793,182 | 12/1988 | Djorup | 73/336.5 |
| 4,898,476 | 2/1990 | Herrmann et al. | 374/28 |
| 5,317,274 | 5/1994 | Nakagawa et al. | 324/678 |
| 5,339,675 | 8/1994 | DiLeo et al. | 73/24.04 |
| 5,364,185 | 11/1994 | Van Zandt et al. | 374/28 |
| 5,476,002 | 12/1995 | Bowers et al. | 73/24.01 |
| 5,531,097 | 7/1996 | Tsuchida et al. | 73/29.02 |

Primary Examiner—Hezron E. Williams
Assistant Examiner—J. David Wiggins
Attorney, Agent, or Firm—Fish & Richardson P.C.

[57] ABSTRACT

A dewpoint/frostpoint hygrometer that uses a surface moisture-sensitive sensor as part of an RF oscillator circuit with feedback control of the sensor temperature to maintain equilibrium at the sensor surface between ambient water vapor and condensed water/ice. The invention is preferably implemented using a surface acoustic wave (SAW) device in an RF oscillator circuit configured to generate a condensation-dependent output signal, a temperature sensor to measure the temperature of the SAW device and to distinguish between condensation-dependent and temperature-dependent signals, a temperature regulating device to control the temperature of the SAW device, and a feedback control system configured to keep the condensation-dependent signal nearly constant over time in the presence of time-varying humidity, corrected for temperature. The effect of this response is to heat or cool the surface moisture-sensitive device, which shifts the equilibrium with respect to evaporation and condensation at the surface of the device. The equilibrium temperature under feedback control is a measure of dewpoint or frostpoint.

54 Claims, 7 Drawing Sheets

FAST, HIGH SENSITIVITY DEWPOINT HYGROMETER

ORIGIN OF INVENTION

The invention described herein was made in performance of work under a NASA contract, and is subject to the provisions Public Law 96-17 (35 U.S.C. 202) in which the contractor has elected to retain title.

BACKGROUND OF THE INVENTION

1. Field of the Invention

This invention relates to electronic sensors, and more specifically to a miniature, solid state electronic hygrometer.

2. Description of Related Art

Water vapor plays a crucial role in energy transport and chemistry in the earth's atmosphere. Accurate measurement of water vapor, or humidity, is crucial to a number of diverse fields, including meteorology, materials processing, manufacturing, and environmental control. These applications require measurement over a very wide range of water vapor concentrations (greater than 1% to less than one part per million by volume), over a large range of ambient temperatures (for example, 170° K. to 500° K.).

Humidity measurement standards developed at NIST (National Institute of Standards and Technology) are based on gravimetric measurements of the water vapor mixing ratio in a gas. However, the instruments used to define these standards are impractical for use in most applications. In practice, there are several different useful measures of humidity for which instruments are available. The most recognized of these measures is relative humidity (RH), which is defined in terms of the mole fraction of water in a specific sample of moist gas relative to the mole fraction at saturation, assuming constant temperature and pressure.

Dewpoint hygrometers are widely used for accurate humidity measurement. Dewpoint is defined as the temperature at which a gas of specific composition is saturated with water vapor, assuming constant pressure. For moist air, steam tables accurately tabulate the water vapor pressure with respect to a planar surface of clean water as a function of water temperature (hence the correlation of dewpoint with water vapor pressure). Similar tables exist for the water vapor pressure with respect to ice, which correlates frost-point to water vapor pressure.

Because of this connection between dewpoint and the thermodynamic properties of water, dewpoint hygrometers have been developed which are sufficiently accurate to be used as transfer standards for humidity measurements.

The unique value of the dewpoint as a measure of humidity is that it provides a direct measurement of the temperature at which a surface will start to collect condensation, and the temperature at which a cloud will begin to form in open air. Further, it has been determined that human comfort is correlated more closely to dewpoint than to relative humidity, because the efficiency of evaporative cooling of human skin is associated with the water vapor pressure in the environment, which is correlated with dewpoint.

Measurement of dewpoint is usually accomplished by apparatus designed to approximate the saturation temperature of air containing an unknown quantity of water vapor. A number of devices (known as hygrometers) for making such measurements exist, including the following instruments:

(1) Commercial hygrometers are known that are based on surface acoustic wave (SAW) devices that detect relative humidity by coating the SAW devices with a hygroscopic material (e.g., a hygroscopic polymer), and measuring the effect of water absorption in the coating on the SAW characteristics. These devices measure relative humidity by using careful calibrations of the water absorption characteristics of the coating and the effects of this absorption on the signal from a coated SAW.

(2) Chilled mirror hygrometers cool a mirror in contact with moist air until a thin layer of condensation forms. The amount of condensation is measured optically by monitoring the reflectivity of the mirror, and the temperature of the mirror is controlled to maintain an equilibrium between condensation and evaporation in the presence of changing humidity. Heating and cooling is typically done by means of thermoelectric coolers, although systems with cryogenic coolers also exist. Chilled mirror hygrometers include feedback control to track dewpoint, and temperature cycling to determine the temperature of the sensor at the onset of condensation. The feedback controller adjusts the mirror temperature to maintain a constant reflectivity in the presence of varying humidity.

(3) U.S. Pat. No. 4,898,476, and references cited therein, disclose hygrometers that detect dewpoint with a device that generates a moisture-dependent electrical signal. Typically these devices use non-resonant capacitive or resistive detectors which are sensitive to condensation. The moisture-dependent signal is kept constant by means of a temperature-controller attached to a heating/cooling device, which is typically a thermoelectric cooler. Typically, a master controller is used to control the moisture-dependent signal by adjusting the value of a desired temperature, and a slave-controller is used to maintain the temperature according to the value set by the master-controller.

(4) U.S. Pat. No. 4,378,168 discloses a hygrometer that uses a non-resonant SAW device to measure the signal attenuation induced by condensation of water on the surface of the device. This reference suggests detecting dewpoint by connecting an RF signal generator to the SAW input and detecting the transmitted RF power at the SAW output in order to generate a signal which is sensitive to condensation.

(5) U.S. Pat. No. 5,364,185, entitled "High Performance Miniature Hygrometer and Method Thereof" and assigned to the assignee of the present invention, discloses a hygrometer comprising an interdigitated transducer, of which a SAW device is an example. This reference teaches that dewpoint measurement from such an instrument is based on determining the second derivative of the moisture-dependent signal with respect to temperature while ramping from a temperature point above the dewpoint to a temperature point below the dewpoint.

A drawback of chilled mirror hygrometers are that they are generally large, complex, expensive, and slow to respond. This precludes their use in a large number of important applications.

Several of the solid state sensor designs have poor sensitivity, exhibit large hysteresis, have limited operating range, and show significant aging effects.

The method shown in U.S. Pat. No. 5,364,185 necessarily produces one measurement of dewpoint/frostpoint per cooling/heating cycle. However, this results in a relatively long time delay while completing such a ramp, which may result in missed data values in a rapidly changing environment, especially considering the relatively long time required to accumulate water in dry environments. In addition, the method of determining dewpoint from the second derivative of the signal may experience problems if humidity changes significantly during the measurement cycle.

It is desirable in certain applications to measure humidity more rapidly and accurately. For example, dewpoint/frostpoint in the external environment of an airplane can change extremely rapidly as the airplane traverses atmospheric structures with a highly non-uniform spatial distribution of water. Examples of these structures include clouds and microbursts, which are important to meteorological studies and airplane safety.

Accordingly, the inventor has perceived a need for an inexpensive, fast, highly sensitive dewpoint hygrometer that overcomes the problems of the prior art. The present invention meets this need.

SUMMARY OF THE INVENTION

The invention comprises a dewpoint/frostpoint hygrometer that uses a surface moisture-sensitive sensor as part of an RF oscillator circuit with feedback control of the sensor temperature to maintain equilibrium at the sensor surface between ambient water vapor and condensed water/ice. The inventive method and apparatus is preferably implemented using a surface acoustic wave (SAW) device in an RF oscillator circuit configured to generate a condensation-dependent output signal, a temperature sensor to measure the temperature of the SAW device and signal conditioning circuit to distinguish between condensation-dependent and temperature-dependent signals, a temperature regulating device to control the temperature of the SAW device, and a feedback control system configured to keep the condensation-dependent signal nearly constant over time in the presence of time-varying humidity, corrected for temperature.

More particularly, the invention uses a surface moisture-sensitive device as a frequency selecting component in an RF oscillator circuit. The moisture-sensitive device acts as a high-Q filter, causing the RF oscillator circuit to oscillate at the resonant frequency of the moisture-sensitive device, which is sensitive to condensation. The amplitude and phase of the output of the RF oscillator circuit also vary with condensation. Dewpoint (or frostpoint, depending on the phase of the condensed moisture) is measured by using a feedback controller to establish equilibrium between evaporation and condensation of moisture on the moisture-sensitive device. In particular, feedback is established by measuring the condensation-dependent signal from the RF oscillator circuit relative to a set point, and generating a response to correct for deviations from the set point. The effect of this response is to heat or cool the moisture-sensitive device, which shifts the equilibrium with respect to evaporation and condensation at the surface of the device. The equilibrium temperature under feedback control is a measure of dewpoint or frostpoint.

In the preferred embodiment, the surface moisture-sensitive device is a SAW device having a high-Q resonance at radio frequencies. The characteristics of the oscillation output (i.e., frequency, amplitude, and phase) of the RF oscillator circuit containing the SAW device are extremely sensitive to condensation on the surface of the SAW device, leading to the ability to measure and respond to very small quantities of condensed water. A temperature sensor thermally coupled to the SAW device is used to measure the temperature of the SAW device, and enable temperature compensation for temperature-induced changes in humidity measurements. Heating and cooling of the moisture-sensitive device (e.g., the SAW device) is done by means of a thermoelectric cooler.

The feedback control system of the invention establishes the required equilibrium with fast response to changes in the condensation-dependent signal, and the surface moisture-sensitive device is responsive to very small changes in the amount of condensed water on its surface during measurements. Coupled with the intrinsic sensitivity and low thermal mass of the preferred SAW sensor, these characteristics result in an extremely fast, highly sensitive dewpoint hygrometer. In experiments comparing the performance of one embodiment of the invention to high-quality chilled-mirror hygrometers, the invention provided significantly faster and more accurate responses to changing humidity conditions.

The details of the preferred embodiment of the invention are set forth in the accompanying drawings and the description below. Once the details of the invention are known, numerous additional innovations and changes will become obvious to one skilled in the art.

BRIEF DESCRIPTION OF THE DRAWINGS

Like reference numbers and designations in the various drawings indicate like elements.

DETAILED DESCRIPTION OF THE INVENTION

Throughout this description, the preferred embodiment and examples shown should be considered as exemplars, rather than as limitations on the invention.

Overview

Figure 1:
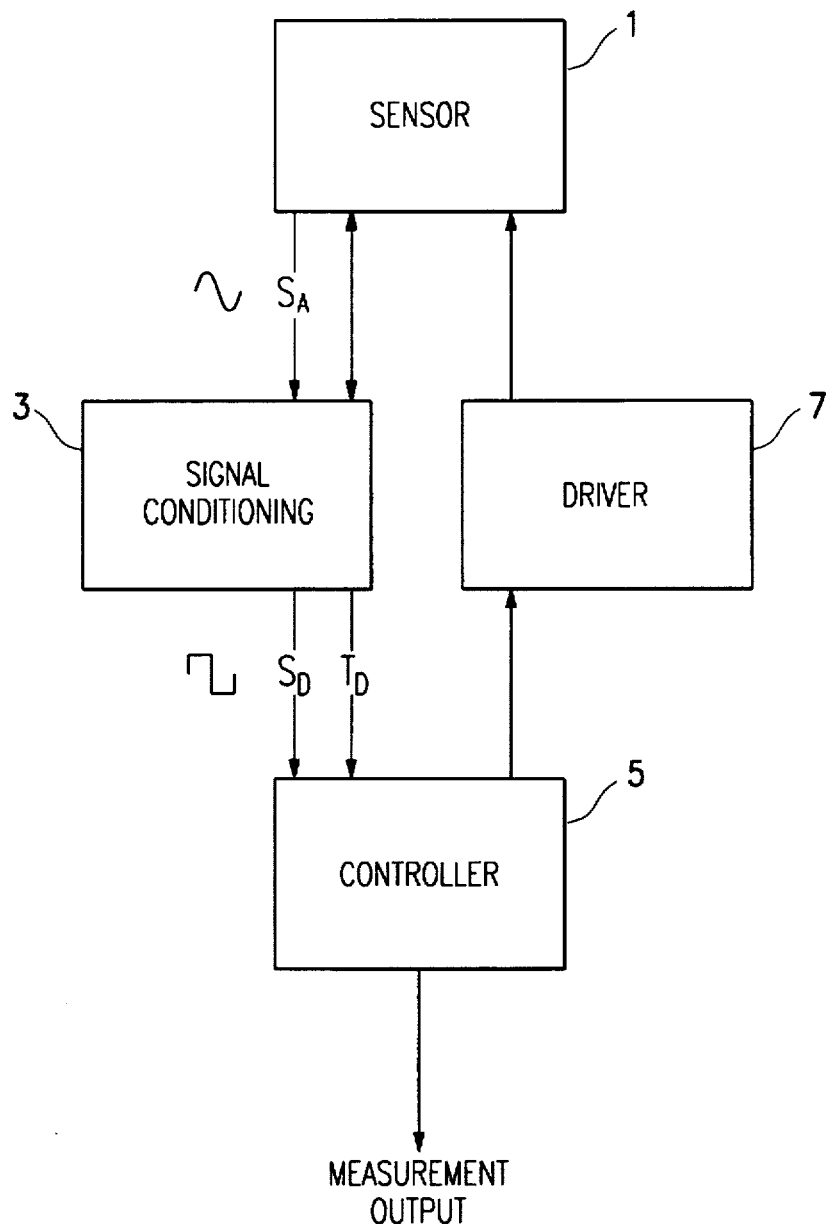
FIG. 1 is a block diagram showing the preferred embodiment of the invention.

FIG. 1 is a block diagram showing a preferred embodiment of the invention. A sensor 1 includes a surface moisture-sensitive device as part of an RF oscillator circuit, a temperature sensor, and a heating/cooling device. The RF oscillator circuit includes the moisture-sensitive device and any combination of inductance, capacitance, resistance, and other electronic elements (passive or active) having such values as to give resonance at RF frequencies. The properties or characteristics of the oscillation output (i.e., frequency, amplitude, mad phase) of the RF oscillator circuit are sensitive to condensation on the surface moisture-sensitive device, producing a condensation-dependent signal. The condensation-dependent output of the sensor 1 is an analog signal $S_A$ varying in response to changes in condensed moisture. In the preferred embodiment, the sensor 1 also provides an analog signal $T_A$ responsive to the temperature of the moisture-sensitive device.

In the embodiment shown, the analog signals from the sensor 1 are coupled to a signal conditioning circuit 3, which preferably converts the analog signals $S_A$, $T_A$ to digital signals $S_D$, $T_D$. Preferably, the signal conditioning circuit 3 also provides any necessary driver signal for the temperature sensor within the sensor 1.

In the preferred embodiment, the condensation-dependent output $S_A$ of the sensor 1 indicates changes in the frequency of the RF oscillator circuit. Accordingly, simply counting the number of digital pulses in $S_D$ in a specific time period provides a direct measurement of the output of the sensor 1, which can be correlated to condensation on the sensor 1. However, any desired frequency measuring circuit can be used to indicate or measure changes in frequency in the RF oscillator circuit induced by surface moisture on the moisture-sensitive device. Further, the output $S_A$ may indicate condensation-dependent changes in the amplitude of the output of the RF oscillator circuit, and/or condensation-dependent changes in the phase of the output of the RF oscillator circuit. Indeed, it is believed that it may be useful to detect condensation-dependent changes in more than one of the three characteristics (frequency, amplitude, and phase) of the oscillation output of the RF oscillator circuit, since such changes may be generated in part in different regimes of environmental conditions. Therefore, these characteristics should not be regarded as wholly equivalent to each other.

The output of the signal conditioning circuit 3 is preferably coupled to a controller 5, which receives the condensation-dependent signal of the moisture-sensitive device and the temperature signal, and calculates a feedback output and a measurement output. In the preferred embodiment, the controller 5 comprises a programmable digital signal processor (DSP) that generates digital output signals.

In the preferred embodiment, a feedback algorithm is implemented in the DSP of the controller 5 to generate an output based on the measured condensation-dependent and temperature signals, pre-programmed calibration parameters, and pre-programmed control parameters. However, an adaptive control system may be used which dynamically determines such parameters. An advantage of using a DSP or similar device as the controller 5 is the flexibility provided for optimizing control of the output by means of software changes, and the freedom to explore complicated control algorithms which would be difficult or impossible in an analog system. A further advantage of this approach is in the ability to communicate with the DSP digitally for the purposes of downloading data or uploading commands. Finally, the use of such processors allows the performance of additional measurements and complex computations on the data, as may be useful in the context of a larger measurement and control system using a dewpoint hygrometer. However, if desired, a completely analog feedback control circuit may be used to regulate the temperature of the moisture-sensitive device in response to changes in the condensation-dependent signal from the RF oscillator circuit.

The controller 5 provides a feedback control output to a driver circuit 7 for the heating/cooling device. The output of the controller 5 is converted by the driver 7 to a current or voltage value which is preferably applied to a thermoelectric heating/cooling device within the sensor 1. However, other electrically controllable temperature regulating devices can be used to control the temperature of the moisture-sensitive device, such as a cold-finger and resistive heater combination in a cryogenic cooling system.

Block Diagram

Figure 2A:
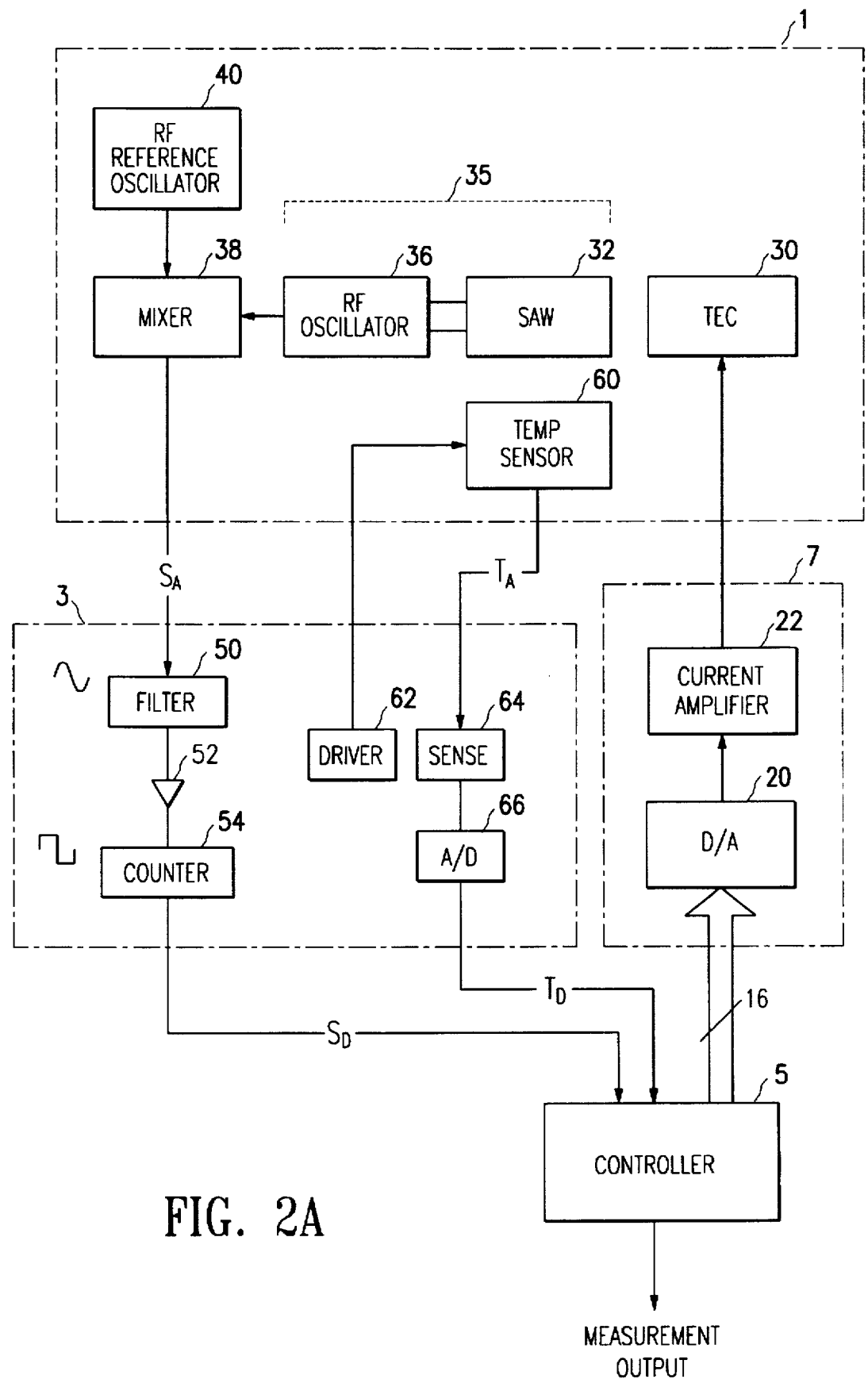
FIG. 2A is a block diagram of the preferred system circuit of the invention.

FIG. 2A is more detailed block diagram of the electronic circuitry of the preferred embodiment of the invention. Dotted-boxes indicate the preferred placement of circuitry within the blocks shown in FIG. 1. However, the actual location of the circuitry is principally a matter of design choice, since most if not all of the system can be implemented as an integrated circuit or hybrid circuit using conventional microelectronics technology.

As shown in FIG. 2A, the feedback control output of the digital controller 5 is coupled by a data bus to a digital-to-analog converter 20 within the driver 7. The output of the digital-to-analog converter 20 is coupled to a current amplifier 22, which in turn is coupled to a thermoelectric cooler 30 of conventional design. The thermoelectric cooler 30 is placed proximate to a SAW device 32 in order to carefully regulate the temperature of the SAW device 32 in response to feedback signals from the controller 5.

The SAW device 32 is the actual moisture sensing device in the sensor 1, and preferably has a high-Q resonance at RF frequencies. A typical Q for a SAW device used in this invention is at least about 2,000–3,000 when loaded. The SAW device 32 may be, for example, an interdigitated transducer (IDT) of the type described in U.S. Pat. No. 5,364,185, which is hereby incorporated by reference.

Figure 2B:
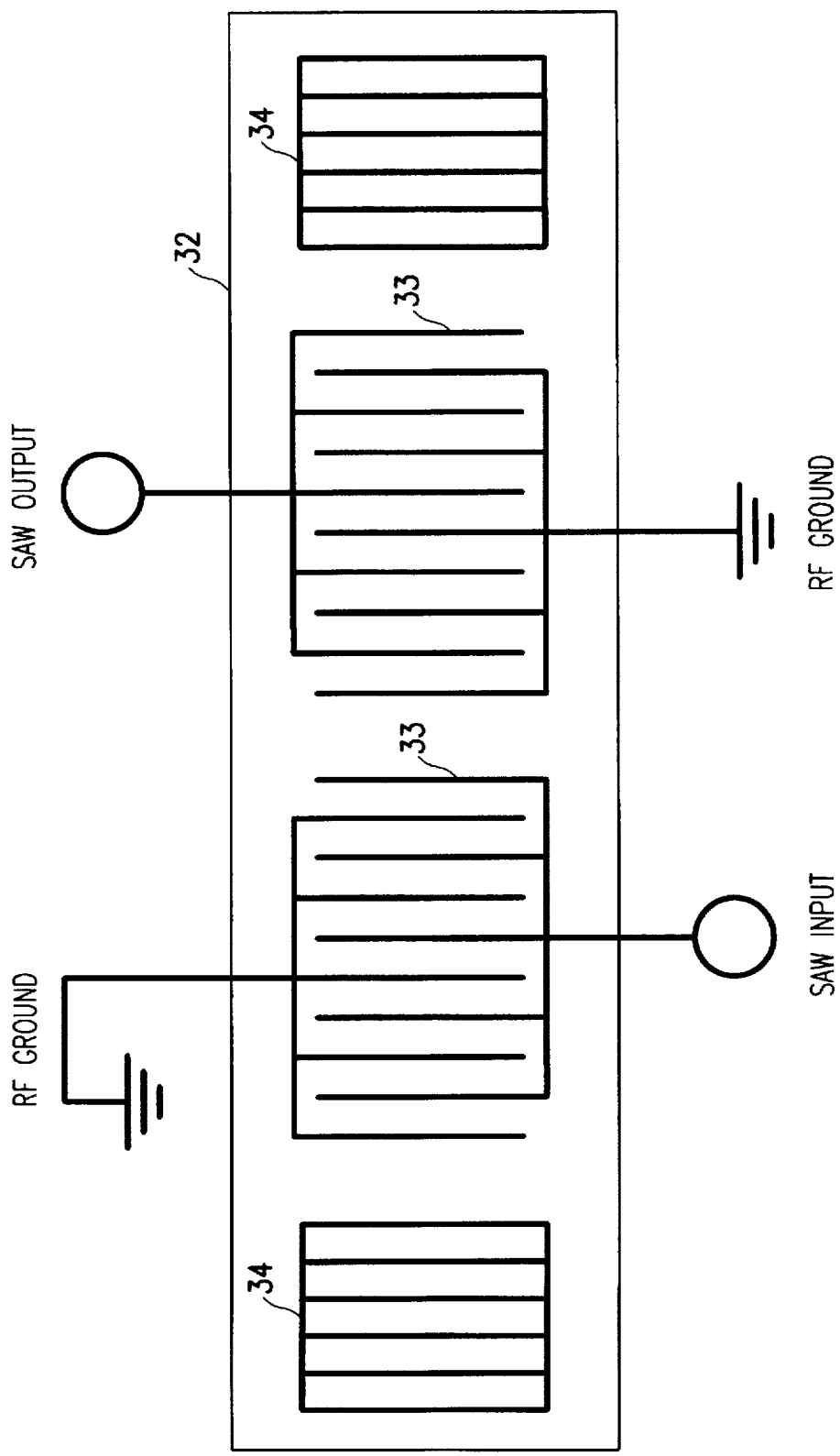
FIG. 2B is a block diagram of the preferred SAW device of the invention.

FIG. 2B is a block diagram of the preferred SAW device of the invention. The IDT SAW device 32 comprises closely spaced pairs of interdigitated electrodes 33 on an insulating piezoelectric (e.g., quartz) substrate. The separation and geometry of the electrodes 33 are designed so as to generate resonant surface acoustic waves in the substrate at a particular frequency. Reflectors 34 located at either end of the SAW device 32 reduce the loss (increase in Q) of the device by preventing loss of energy from the ends of the device. These characteristics allow the formation of acoustic delay lines and resonators which are sensitive to moisture due to the strong interaction of the surface wave with an adsorbed water layer. In the case of a SAW resonator, the device's resonant frequency is dependent upon water loading: adsorbed water alters the acoustic propagation of the SAW device 32, resulting in acoustic loss between the input and output of the device. This results in changes in resonator output characteristics such as frequency, phase, and amplitude. While an IDT structure is preferred for the SAW device 32, other moisture-sensitive SAW structures can be used as well.

Importantly, the SAW device 32 is the frequency selecting component of an RF oscillator circuit 35. In the preferred embodiment, the oscillation frequency of the RF oscillator circuit 35 is output as the condensation-dependent signal $S_A$ of the sensor 1. This oscillation frequency is extremely sensitive to condensation on the surface of the SAW device 32, leading to the ability to measure and respond to very small quantities of condensed water. This sensitivity results in fast response, because the time required to accumulate water from the air can be a limiting factor in response time, particularly under conditions of very low dewpoint or frostpoint. In addition, the low thermal mass of the SAW device 32 results in the ability to change the temperature of the SAW device 32 very quickly, further contributing to the fast response of the invention. Further, the amplitude and phase of the output of the RF oscillator circuit 35 also vary with condensation. Thus, measurement of changes in either or both of these characteristics can be used in place of, or to supplement, measurement of changes in frequency output.

More particularly, in the preferred embodiment, the RF oscillator circuit 35 consists of an RF feedback oscillator 36 and a SAW device 32 which establishes the oscillation frequency of the RF oscillator circuit 35. The RF feedback oscillator 36 may be, for example, an amplifier having its input coupled to the output of the SAW device 32, and its output fed back to the input of the SAW device 32, together with phase-matching components and filters. Other RF oscillator circuits can be used that output a signal responsive to the output of a moisture-sensitive device, particularly a SAW device 32.

In the preferred embodiment, the output of the RF oscillator circuit 35 is coupled to a frequency down-converter comprising an RF mixer circuit 38 and an RF reference frequency source 40. The RF mixer circuit 38 generates a frequency output as the difference between the output frequency of the RF oscillator circuit 35 and the RF reference frequency source 40.

The output signal of the RF mixer circuit 38 is coupled to the signal conditioning circuitry 3, comprising a filter 50, an amplifier circuit 52, and a counter 54, which converts the sinusoidal output of the RF mixer circuit 38 to a variable-frequency digital signal (e.g., a standard 5 volt TTL signal) and outputs a digital frequency count F. The digital frequency count F is then coupled to the controller 5. Alternatively, the frequency of the digital signal from the amplifier 52 is measured via other hardware circuitry or by a software-implemented frequency counter in the DSP within the controller 5.

A shift in the frequency of the RF oscillator circuit 35 containing the SAW device 32 generates an identical frequency shift in the digital signal, with the advantage that the digital signal is at a much lower frequency after down-conversion and is therefore easier to measure. The shift in frequency of the digital signal caused by condensation of moisture on the SAW device 32 correlates to condensation. The controller 5 outputs a measurement output that indicates the measured equilibrium temperature of the SAW device 32, which corresponds to a constant frequency shift. This value can be correlated to humidity level of an ambient gas at the measured temperature.

Figure 2C:
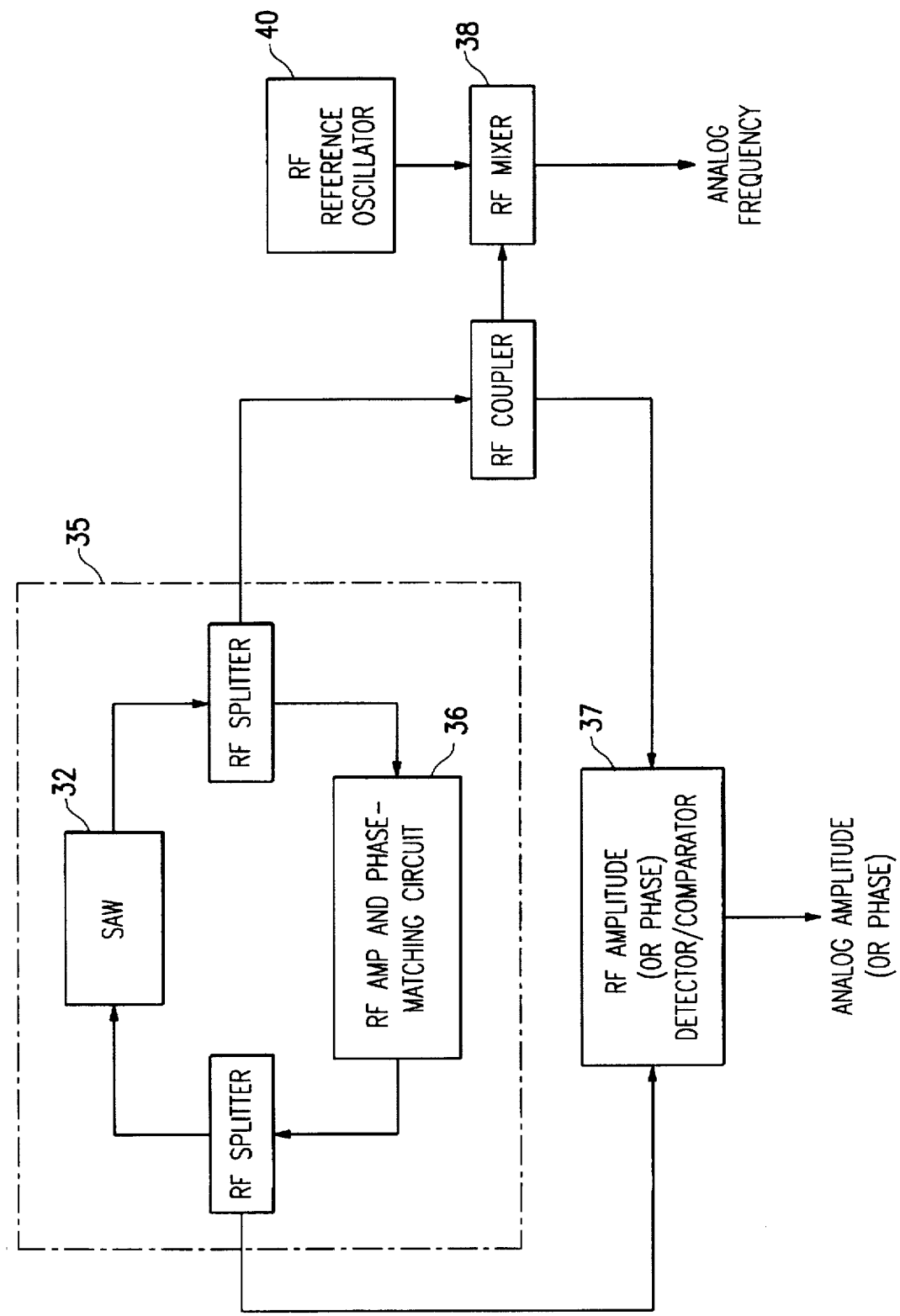
FIG. 2C is a block diagram of an alternative RF oscillator circuit for the invention.

In addition to, or instead of, measurement of changes in frequency of the RF oscillator circuit 35, changes in phase and/or amplitude of the RF signal measured at the output of the SAW device 32 versus the RF signal measured at the input of the SAW device 32 due to condensation on the SAW device 32 can be correlated to humidity level. For example, FIG. 2C is a block diagram of an alternative RF oscillator circuit for the invention. While the basic circuit is the same as shown in FIG. 2A, RF splitters and an RF coupler are positioned as shown to allow an RF amplitude or phase detector/comparator circuit 37 to be coupled across the SAW device 32. This configuration allows the detector/comparator circuit 37 to measure changes in the phase and/or amplitude across the SAW device 32 due to condensation on the SAW device 32.

The feedback control provided by the controller 5 is used to track time-varying humidity by detecting changes in signal from the moisture-sensitive device (i.e., SAW device 32) in the sensor 1, and adjusting the temperature of the sensor to compensate for the change. When operating properly, the controller 5 varies the temperature of the SAW device 32 to keep the condensation-dependent signal nearly constant. A constant signal indicates that an equilibrium has been established between vapor pressure of the condensed water and the ambient water vapor pressure (i.e., the rate of evaporation is equal to rate of condensation). The measured temperature of the SAW device 32 at equilibrium indicates the humidity level of the ambient atmosphere or gas.

In order to provide temperature measurement, a temperature sensor 60 is also provided within the sensor 1. The temperature sensor 60 may be, for example, a thermistor, or temperature sensitive transistor, or other temperature sensitive device. However, in the preferred embodiment, the temperature sensor 60 comprises a resistor which is mounted proximate to the SAW device 32 or integrated on the SAW device 32 itself and coupled to a current source driver 62 and a voltage-sensing circuit 64. The current source driver 62 applies a fixed, small current through the resistor sensor 60, while the voltage-sensing circuit 64 measures the voltage across the resistor. Measurement of this voltage constitutes a temperature measurement $T_A$, in that voltage is proportional to the resistance, which depends monotonically on the temperature of the resistor sensor 60. The output of the voltage-sensing circuit 64 is applied to an analog-to-digital converter 66 which supplies a digital temperature signal $T_D$ to the controller 5.

In principle, the temperature where equilibrium is established constitutes a measurement of dewpoint (or frostpoint, depending on the phase of the condensed water). In practice, the equilibrium temperature may deviate somewhat from the actual dewpoint/frostpoint, with an error that depends on such variables as the feedback parameters, contamination of the SAW device 32, flow rate of gas over the SAW device 32, etc. Furthermore, in practice, transient changes in humidity will cause deviations from equilibrium, which constitutes an error in measurement. However, such transient errors are minimized by the use of the SAW device 32 as a sensitive moisture sensor, and optimal choice of feedback characteristics with respect to overshoot and settling time. The techniques of selecting such optimal parameters are well-known.

While the feedback loop of the invention includes means to heat and cool the SAW device 32 in order to maintain equilibrium, this method is distinct from a temperature controller in that the controlled parameter is the condensation-dependent signal. The feedback loop is independent of the temperature measurement because changes in the controlled parameter (the condensation-dependent signal) are used to directly generate the output of the controller 5 to the TEC (thermoelectric cooler) driver 7.

Temperature Compensation

The condensation-dependent signal $S_D$ coupled to the controller 5 depends on both sensed moisture (i.e., condensation) and the temperature of the moisture-sensitive device in the sensor 1. An improvement in the performance of the invention results from separating the effects of temperature and condensation. This improvement has been implemented in the preferred embodiment by measuring the condensation-dependent output of the RF oscillator circuit 35 as a function of the temperature of the SAW device 32 while flowing dry nitrogen over the SAW device 32. This data can be easily fitted to a polynomial function to give a calibrated reference curve that closely approximates the output of the RF oscillator circuit 35 as a function of the temperature of the SAW device 32 when the surface of the SAW device 32 is completely dry.

Using the measured temperature of the SAW device 32, this calibration can be used to calculate the expected output characteristics of the RF oscillator circuit 35 for a dry SAW device 32 at that temperature (the frequency, amplitude, and/or phase characteristic or property calculated from the calibrated reference curve is referred to as the "dry environment value"). Subtraction of the measured condensation-dependent signal from the dry environment value gives a corrected value, which can be attributed to condensation on the surface SAW device 32.

Thus, for example, the measured temperature of the SAW device 32 is used to compensate the condensation-dependent output of the RF oscillator circuit 35 for thermal dependence of SAW device 32 characteristics. This compensation distinguishes frequency, amplitude, and/or phase output signal changes due to condensed water (i.e., a condensation-dependent component) from signal changes due to temperature (i.e., a temperature-dependent component), thereby improving the performance of the sensor 1 by enabling operation over a larger dynamic range.

Figure 3:
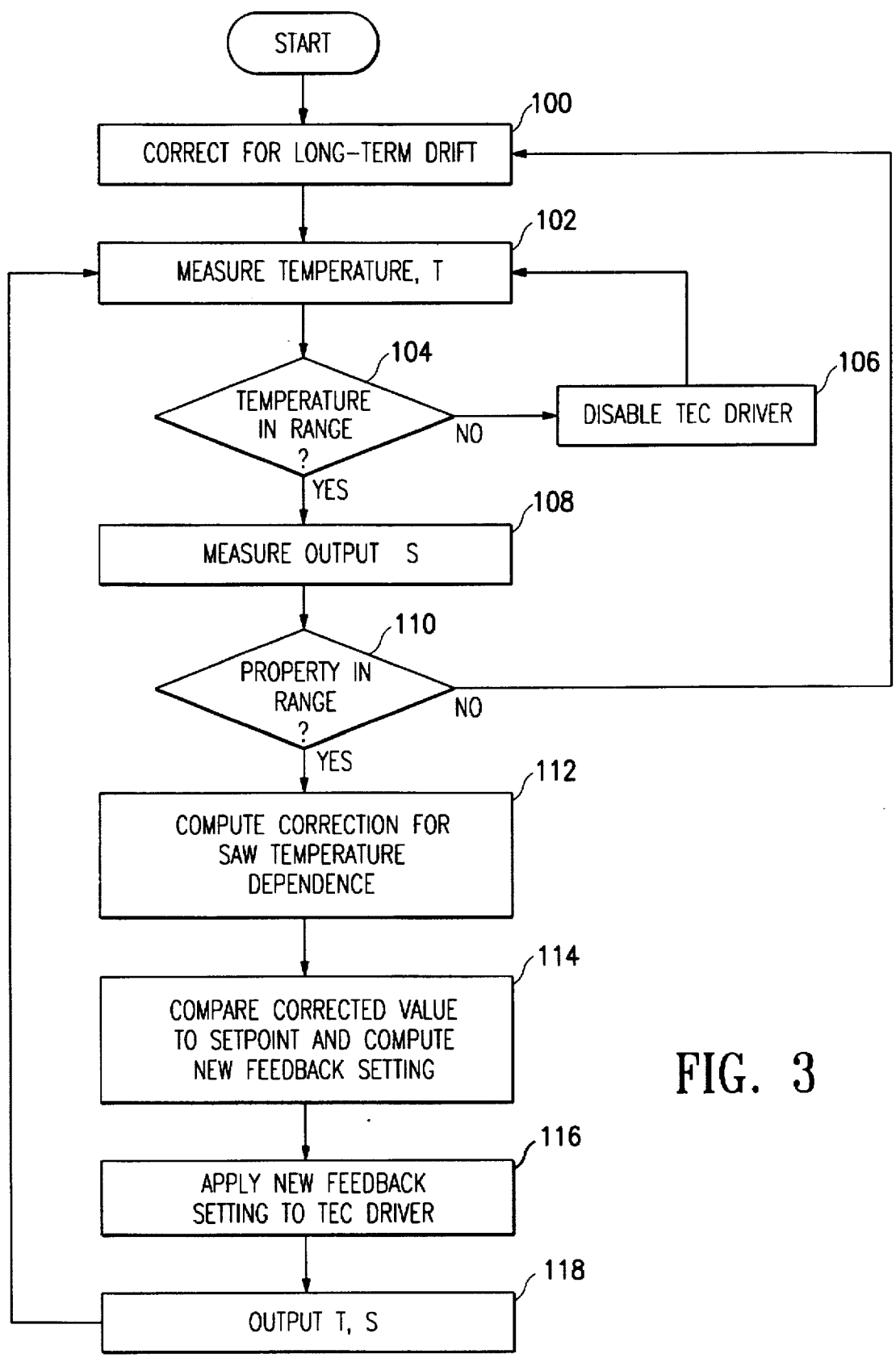
FIG. 3 is a flowchart showing the preferred feedback algorithm of the invention.

FIG. 3 is a flowchart showing the preferred feedback algorithm of the invention, which incorporates compensation of the output of the RF oscillator circuit 35 for temperature dependence of the resonant properties of the SAW device 32. Prior to initiation of the algorithm, the output of the RF oscillator circuit 35 is measured as a function of the temperature of the SAW device 32, with precautions taken to keep the surface of the SAW device 32 dry. Typically, the SAW device 32 is exposed to flowing dry nitrogen, and the temperature of the SAW device 32 is ramped through the thermal range of the instrument, starting at the highest temperature of the measurement range and slowly ramping the temperature down to the lowest temperature of the measurement range while periodically making simultaneous measurements of the SAW temperature and the output of the RF oscillator circuit 35. This data is then fitted to a polynomial function, and the parameters for the polynomial fit are stored in memory and accessed during operation of the invention.

Figure 4:
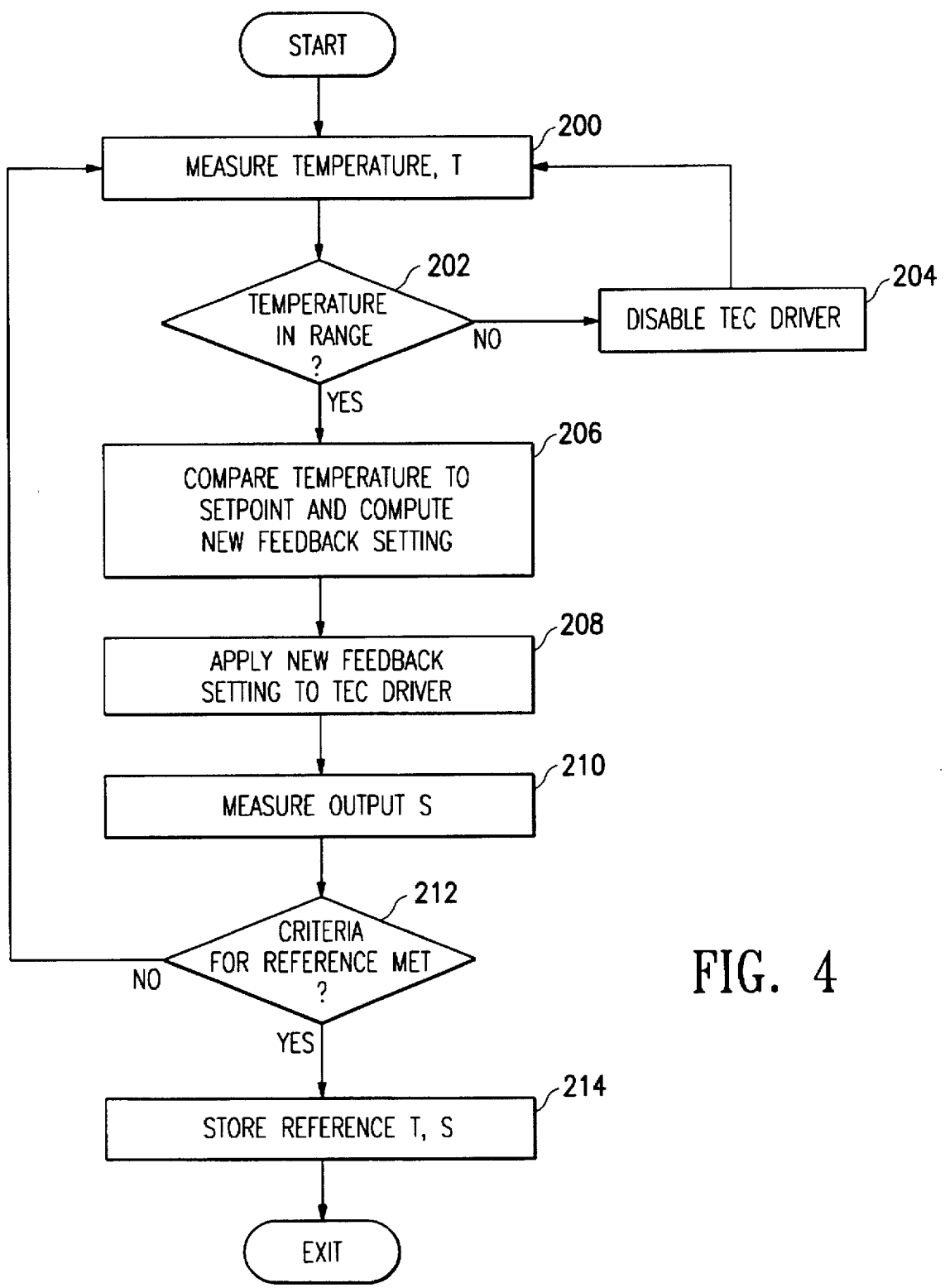
FIG. 4 is a flowchart showing the preferred algorithm of the invention for obtaining a reference point or set point for measurements of the output of the RF oscillator circuit. The reference measurement is used to correct for long-term drift in the sensor or measurement electronics.
Figure 5:
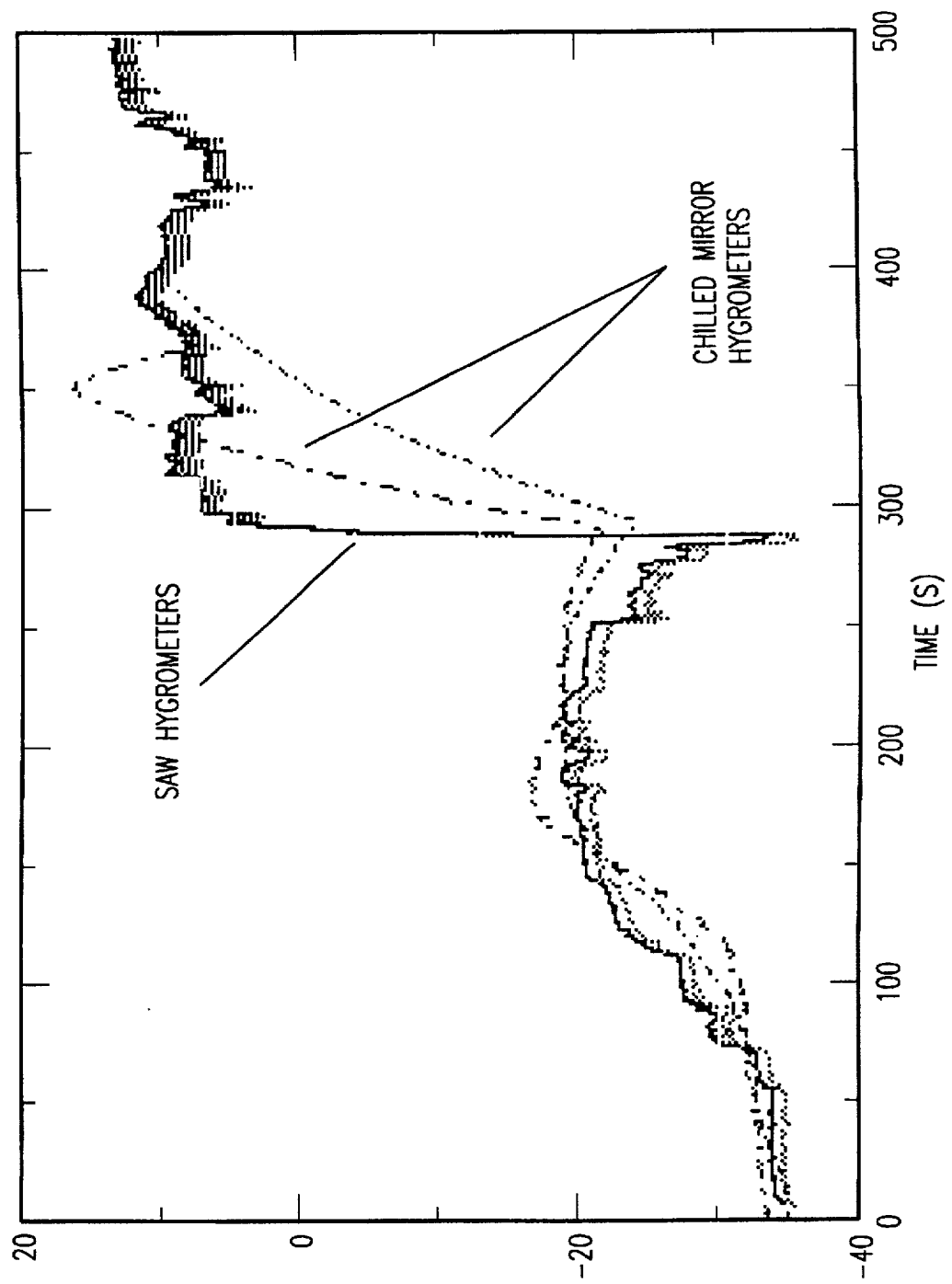
FIG. 5 is a graph comparing humidity data versus time taken by two chilled mirror hygrometers and two hygrometers fabricated in accordance with the invention.

At the start of the feedback algorithm, the SAW device 32 is heated and a reference point for temperature compensation is measured (STEP 100). The detailed algorithm for measuring the reference point is shown in FIG. 4, and discussed in detail below. Following measurement of the reference point, the main loop of the feedback control algorithm is entered. Feedback control begins with measuring the temperature of the SAW device 32 (STEP 102) to determine whether a fault condition exists. If the temperature is out of range (STEP 104), the TEC driver 7 is disabled as a precaution against overheating, which could cause damage to the sensor (STEP 106). The algoriyhm then loops while the temperature is repeatedly measured (STEP 102) and tested (STEP 104) until an acceptable temperature is measured.

After an acceptable temperature is measured, the output S of the RF oscillator circuit 35 is measured (STEP 108). If the output of the RF oscillator circuit 35 is out of range (STEP 110), the algorithm returns to the beginning (STEP 100), and a new reference point is measured. Because measurement of the reference point involves heating the SAW device 32 to evaporate condensed moisture, this procedure allows the instrument to recover from excessive condensation on the SAW device 32, which is the most common cause for out-of-range values of the output of the RF oscillator circuit 35.

If the output S of the RF oscillator is within the range of acceptable values, the measured output is corrected for temperature dependence using the pre-determined calibration parameters and the most recently measured reference point, in order to determine the component of the signal which is due to condensation on the SAW device 32 (STEP 112). In the preferred embodiment, the corrected output $S_{corr}$ is computed as follows: $S_{corr}=S_{measured}-S_{cal}$, where $S_{cal}$ is a function of temperature and the dry environment calibration curve. The corrected output $S_{corr}$ is stored for use in subsequent iterations of the feedback algorithm.

The corrected output $S_{corr}$ is then used to derive a new feedback setting for the driver 7 of the thermoelectric cooler 30 (STEP 114). The new value for the feedback setting is computed based on measurements in the current and previous iterations, according to an algorithm which determines the specific type of feedback controller which characterizes the overall feedback algorithm. An example of such an algorithm is a PID controller, which applies proportional, integral, and differential terms to calculate the output of the controller 5 from the input. However, any type of feedback controller which provides stable control of the output of the RF oscillator circuit 35 may be used in this invention. The new feedback setting is then applied to the driver 7 (STEP 116).

Lastly, the measured temperature and output values, T and S, are transferred to data storage, display, or communications ports as appropriate (STEP 118), and the algorithm returns to the beginning of the main feedback loop at STEP 102 for another measurement/control cycle.

Provided that the parameters for the controller 5 have been well-chosen with regard to the time constants of the sensor 1, this algorithm will cause the temperature of the SAW device 32 to stabilize at a temperature corresponding to a constant amount of condensed moisture on the surface of the SAW device 32. The measured temperature, which at equilibrium is equal to dewpoint or frostpoint depending on the phase of the condensed moisture, depends on the humidity and is reported as the output of the instrument.

More or fewer steps can be taken in performing the algorithm described in FIG. 3. For example, the steps for determining whether a fault condition exists may be omitted.

There are a number of aspects of instrument design, such as the use of a sampling system constructed with appropriate materials, techniques, and flow rates, which are known and should be applied to ensure that the measured temperature accurately reflects the humidity in the environment.

Reference Point Determination

As a Further refinement to the temperature compensation technique, the SAW device 32 is periodically heated well above the dewpoint to drive condensed water from its surface. The elevated temperature is preferably maintained until the output of the RF oscillator circuit 35 is stable, thus indicating that the surface of the SAW device 32 is dry. The output of the RF oscillator circuit 35 is then measured, providing a "known dry" reference measurement. By utilizing this reference measurement, long-term drift in the calibration of the sensor 1 due to a variety of causes can be ameliorated with a simple in situ measurement.

FIG. 4 is a flowchart showing the preferred algorithm for obtaining a reference point for measurements of the output of the RF oscillator circuit 35. This reference point is used in the main feedback algorithm for temperature compensation of the measured output of the RF oscillator circuit 35. In addition, periodic application of this algorithm to obtain a new reference point can be used to correct for long-term drift in the measured output of the RF oscillator circuit 35. This algorithm can also be used to recover from pathologic conditions, as might be experienced when excessive condensation forms on the surface of the SAW device 32, interfering with the normal operation of the RF oscillator circuit 35.

The algorithm incorporates a temperature feedback controller, which adjusts the temperature of the SAW device 32 to some pre-determined setpoint, chosen to be far enough above dewpoint to ensure that the surface of the SAW device 32 is dry. At the start of the algorithm, the temperature of the SAW device 32 is measured (STEP 200), and compared with an acceptable range for the temperature of the SAW device 32 (STEP 202). If the temperature of the SAW device 32 is outside of this range, the TEC driver is disabled as a precaution against overheating the sensor (STEP 204), and the temperature of the SAW device 32 is again measured (STEP 200). The algorithm remains within this loop until an acceptable temperature measurement is obtained.

Once the temperature is determined to be in an acceptable range (STEP 202), the measured temperature is compared with a temperature setpoint, chosen to be well above the dewpoint, to derive a new feedback setting for the driver 7 of the thermoelectric cooler 30 (STEP 206). The difference between these values is stored for use in subsequent iterations of this feedback algorithm. The new value for the feedback output is computed based on measurements in the current and previous iterations, according to an algorithm which determines the specific type of feedback controller which characterizes this overall feedback algorithm. An example of such an algorithm is a PID controller, which applies proportional, integral, and differential terms to calculate the output of the controller 5 from the input. However, any type of feedback controller which provides stable control of the SAW temperature may be used in this invention.

The new feedback setting is then applied to the TEC driver 7 (STEP 208). Each pass through this algorithm, the feedback setting is updated according to the latest temperature measurement, and, with pre-determined feedback parameters chosen for stable operation of this algorithm, the temperature of the SAW device 32 will stabilize at a temperature close to the desired setpoint.

After updating the output to the TEC driver 7, the output S of the RF oscillator circuit 35 is measured (STEP 210) and a determination is made as to whether the criteria for a good reference measurement have been met (STEP 212). Such criteria could be length of time at the desired temperature, or a requirement that the measured values have stabilized. If the criteria are not met, then the algorithm repeats at STEP 200. If the criteria are met, then the measured temperature and output values, T and S, are stored as new reference points (STEP 214), and the controller 5 exits the algorithm.

More or fewer steps can be taken in performing the algorithm described in FIG. 4. For example, the steps for determining whether a fault condition exists may be omitted.

Experimental Results

A dewpoint hygrometer constructed in accordance with the teachings above was tested in a laboratory humidity generator and on the NASA DC8 Airborne Laboratory and compared with commercial chilled mirror hygrometers. Laboratory comparisons showed that the steady-state accuracy of the invention was comparable to the chilled mirror hygrometers. This result is significant, because chilled mirror hygrometers are accepted tools for accurate measurement of dewpoint in a variety of important applications. Measurements in the laboratory also showed that the invention responded significantly faster (e.g., more than about 10 times faster, in some cases) to humidity transients then the chilled mirror hygrometers. This result was even more dramatic in tests performed during airplane flights.

The NASA DC8 Airborne Laboratory is a modified commercial aircraft used as an experimental platform for a variety of scientific projects. The facility instruments on the aircraft include two commercial chilled mirror hygrometers configured to sample air external to the aircraft and to measure dewpoint/frostpoint during flight. Two dewpoint hygrometers embodying the invention were mounted in the aircraft to independently measure humidity external to the aircraft. An example of data taken during the descent of the aircraft is shown in the graph of FIG. 4, which illustrates the superior performance of the invention. By comparing the signals from the invention with the chilled mirror hygrometers, it is possible to evaluate the accuracy and speed of response of the invention in comparison with the chilled mirror technology. Furthermore, analysis of the independent data from the two inventive hygrometers allows features in the data due to the variation of humidity to be distinguished from random measurement errors, thus providing a way to validate the data.

These measurements showed that the inventive hygrometers exhibited response time more than an order of magnitude faster than the chilled mirror hygrometers, with a resulting improvement in accuracy in measuring humidity in a dynamic environment. Relative to the inventive hygrometers, the chilled mirror hygrometers exhibited sluggish response, large errors, and hysteresis due to transient effects. In particular, the inventive hygrometers were able to record structure in the atmospheric humidity which was completely missed by the slower-responding chilled mirror hygrometers.

Implementation

The feedback and compensation algorithms of the invention may be implemented in hardware or software, or a combination of both. However, preferably, the algorithms are implemented in computer programs executing on programmable computers each comprising at least one processor, a data storage system (including volatile and non-volatile memory and/or storage elements), at least one input device, and at least one output device. Program code is applied to input data to perform the functions described herein and generate output information. The output information is applied to one or more output devices, in known fashion.

Each such program is preferably implemented in a high level procedural or object oriented programming language to communicate with a computer system. However, the programs can be implemented in assembly or machine language, if desired. In any case, the language may be a compiled or interpreted language.

Each such computer program is preferably stored on a storage media or device (e.g., ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

Summary

The feedback control system of the invention establishes equilibrium with fast response to changes in the condensation-dependent signal, and the moisture-sensitive device is responsive to very small changes in the amount of condensed water during measurements. Coupled with the intrinsic sensitivity and low thermal mass of the preferred SAW sensor, these characteristics result in an extremely fast, highly sensitive dewpoint hygrometer. Further, the invention can be fabricated at low cost relative to such devices as chilled mirror hygrometers and used in more applications.

A number of embodiments of the invention have been described. Nevertheless, it will be understood that various modifications may be made without departing from the spirit and scope of the invention. Accordingly, it is to be understood that the invention is not to be limited by the specific illustrated embodiment, but only by the scope of the appended claims.

The invention claimed is:

1. A device for measuring humidity, comprising:
   (a) an RF oscillator circuit including a resonant moisture-sensitive device having a surface that is essentially non-hygroscopic, sensitive to moisture in an ambient gas and subject to condensation of moisture from the gas onto the surface, the RF oscillator circuit being configured to generate a condensation-dependent signal indicative of the amount of condensation on the surface of the resonant moisture-sensitive device;
   (b) a temperature regulating device, proximate to the resonant moisture-sensitive device, for controlling the temperature of the resonant moisture-sensitive device;
   (c) a controller, coupled to the output of the RF oscillator circuit and to the temperature regulating device, for:
      (1) monitoring the condensation-dependent signal of the RF oscillator circuit; and
      (2) generating a feedback signal to the temperature regulating device responsive to changes in the condensation-dependent signal relative to a set point, the feedback signal controlling the amount of condensation on the resonant moisture-sensitive device by governing the temperature regulating device used for controlling the temperature of the resonant moisture-sensitive device;
   (d) a temperature sensor, proximate the resonant moisture-sensitive device, for measuring the temperature of the resonant moisture-sensitive device and generating an output signal indicative of the amount of moisture in the gas.

2. The device of claim 1, wherein the temperature sensor is coupled to the controller, and wherein the controller is further for correcting the feedback signal in response to the measured temperature of the resonant moisture-sensitive device so as to substantially remove a temperature-dependent component from the condensation-dependent signal.

3. The device of claim 1, wherein the temperature sensor comprises:
   (a) a resistor;
   (b) a current source, coupled to the resistor, for supplying a constant current flow through the resistor;
   (c) a voltage-sensing circuit, coupled across the resistor, for measuring voltage across the resistor from current flowing through the resistor, such voltage varying with temperature, and for generating a signal indicative of such temperature.

4. The device of claim 1, wherein the condensation-dependent signal indicates a change in frequency of the RF oscillator circuit.

5. The device of claim 1, wherein the condensation-dependent signal indicates a change in amplitude of the RF oscillator circuit.

6. The device of claim 1, wherein the condensation-dependent signal indicates a change in phase of the RF oscillator circuit.

7. The device of claim 1, wherein the temperature regulating device is a thermoelectric cooler.

8. The device of claim 1, wherein the condensation-dependent signal has an analog form, and further including a signal conditioning circuit coupled to the output of the RF oscillator circuit and to an input to the controller, for converting the condensation-dependent signal from analog form to digital form.

9. The device of claim 1, further including means for periodically elevating the temperature of the resonant moisture-sensitive device above the dewpoint and measuring the condensation-dependent signal at such elevated temperature to provide a reference level signal for the device for measuring humidity.

10. The device of claim 1, wherein the resonant moisture-sensitive device is a resonant surface acoustic wave device.

11. The device of claim 1, wherein the resonant moisture-sensitive device has a high Q value.

12. The device of claim 11, wherein the Q value exceeds about 2,000.

13. A device for measuring humidity, comprising:
   (a) an RF oscillator circuit, including a resonant surface acoustic wave device having a high Q value and a surface that is essentially non-hygroscopic, sensitive to moisture in an ambient gas and subject to condensation from the gas onto the surface, the RF oscillator circuit being configured to generate a condensation-dependent signal indicative of the amount of condensation on the surface of the resonant surface acoustic wave device;
   (b) a temperature regulating device, proximate to the resonant surface acoustic wave device, for controlling the temperature of the resonant surface acoustic wave device;
   (c) a controller, coupled to the output of the RF oscillator circuit and to the temperature regulating device, for:
      (1) monitoring the condensation-dependent signal of the RF oscillator circuit; and
      (2) generating a feedback signal to the temperature regulating device responsive to changes in the condensation-dependent signal relative to a set point, the feedback signal controlling the amount of condensation on the resonant surface acoustic wave device by governing the temperature regulating device used for controlling the temperature of the resonant surface acoustic wave device;
   (d) a temperature sensor, proximate the resonant surface acoustic wave device, for measuring the temperature of the resonant surface acoustic wave device and generating an output signal indicative of the amount of moisture in the gas.

14. The device of claim 13, wherein the temperature sensor is coupled to the controller, and wherein the controller is further for correcting the feedback signal in response to the measured temperature of the resonant surface acoustic wave device so as to substantially remove a temperature-dependent component from the condensation-dependent signal.

15. The device of claim 13, wherein the temperature sensor comprises:
   (a) a resistor;
   (b) a current source, coupled to the resistor, for supplying a constant current flow through the resistor;
   (c) a voltage-sensing circuit, coupled across the resistor, for measuring voltage across the resistor from current flowing through the resistor, such voltage varying with temperature, and for generating a signal indicative of such temperature.

16. The device of claim 13, wherein the condensation-dependent signal indicates a change in frequency of the RF oscillator circuit.

17. The device of claim 13, wherein the condensation-dependent signal indicates a change in amplitude of the RF oscillator circuit.

18. The device of claim 13, wherein the condensation-dependent signal indicates a change in phase of the RF oscillator circuit.

19. The device of claim 13, wherein the temperature regulating device is a thermoelectric cooler.

20. The device of claim 13, wherein the condensation-dependent signal has an analog form, and further including a signal conditioning circuit coupled to the output of the RF oscillator circuit and to an input to the controller, for converting the condensation-dependent signal from analog form to digital form.

21. The device of claim 13, further including means for periodically elevating the temperature of the resonant surface acoustic wave device above the dewpoint and measuring the condensation-dependent signal at such elevated temperature to provide a reference level signal for the device for measuring humidity.

22. The device of claim 13, wherein the Q value of the resonant surface acoustic wave device exceeds about 2,000.

23. An electronic hygrometer comprising:
  (a) an RF oscillator circuit, including a resonant surface acoustic wave device having a high Q value and a surface that is essentially non-hygroscopic, sensitive to moisture in an ambient gas and subject to condensation from the gas onto the surface, the RF oscillator circuit being configured to generate a condensation-dependent signal directly dependent on the amount of condensation on the surface of the resonant surface acoustic wave device;
  (b) a thermoelectric cooler, proximate to the resonant surface acoustic wave device, for controlling the temperature of the resonant surface acoustic wave device;
  (c) a temperature sensor, proximate the resonant surface acoustic wave device, for measuring the temperature of the resonant surface acoustic wave device and for generating an output signal indicative of the amount of moisture in the gas;
  (d) a controller, coupled to the output of the RF oscillator circuit, the thermoelectric cooler, and the temperature sensor, for:
    (1) monitoring the condensation-dependent signal of the RF oscillator circuit; and
    (2) generating a feedback signal to the temperature regulating device responsive to changes in the condensation-dependent signal relative to a set point, the feedback signal controlling the amount of condensation on the resonant surface acoustic wave device by governing the thermoelectric cooler used for controlling the temperature of the resonant surface acoustic wave device; and
    (3) correcting the feedback signal in response to the measured temperature of the resonant surface acoustic wave device so as to substantially remove a temperature-dependent component from the condensation-dependent signal.

24. The electronic hygrometer of claim 23, wherein the condensation-dependent signal has an analog form, and further including a signal conditioning circuit coupled to the output of the RF oscillator circuit and to an input to the controller, for converting the condensation-dependent signal from analog form to digital form.

25. The electronic hygrometer of claim 23, further including means for periodically elevating the temperature of the resonant surface acoustic wave device above the dewpoint and measuring the condensation-dependent signal at such elevated temperature to provide a reference level signal for the electronic hygrometer.

26. A device responsive to changes in humidity, comprising:
  (a) an RF oscillator circuit, including an oscillator circuit and a resonant moisture-sensitive device having a surface that is essentially non-hygroscopic, sensitive to moisture in an ambient gas and subject to condensation of moisture from the gas onto the surface, configured to generate a condensation-dependent signal indicative of the amount of condensation on the surface of the resonant moisture-sensitive device;
  (b) a temperature regulating device, proximate to the resonant moisture-sensitive device, for controlling the temperature of the resonant moisture-sensitive device;
  (c) a controller, coupled to the output of the RF oscillator circuit and to the temperature regulating device, for:
    (1) monitoring the condensation-dependent signal of the RF oscillator circuit; and
    (2) generating a feedback signal to the temperature regulating device responsive to changes in the condensation-dependent signal relative to a set point, the feedback signal controlling the amount of condensation on the resonant moisture-sensitive device by governing the temperature regulating device used for controlling the temperature of the resonant moisture-sensitive device.

27. The device of claim 26, wherein the resonant moisture-sensitive device is a resonant surface acoustic wave device having a characteristic Q value.

28. The device of claim 27, wherein the Q value of the resonant surface acoustic wave device exceeds about 2,000.

29. The device of claim 26, wherein the resonant moisture-sensitive device has a high Q value.

30. The device of claim 29, wherein the Q value of the resonant moisture-sensitive device exceeds about 2,000.

31. A method for measuring humidity, comprising the steps of:
  (a) measuring a condensation-dependent signal output by an RF oscillator circuit including a resonant moisture-sensitive device having a surface that is essentially non-hygroscopic, sensitive to moisture in an ambient gas and subject to condensation of moisture from the gas onto the surface, the condensation-dependent signal being indicative of the amount of condensation on the surface of the resonant moisture-sensitive device;
  (b) monitoring the condensation-dependent signal of the RF oscillator circuit;
  (c) comparing changes in the condensation-dependent signal relative to a set point;
  (d) regulating the temperature of the resonant moisture-sensitive device in response to such changes so as to maintain equilibrium at the surface of the resonant moisture-sensitive device between moisture in the gas and moisture condensed on the surface of the resonant moisture-sensitive device;
  (e) measuring the temperature of the moisture-sensitive device;
  (f) generating an output signal, indicative of the amount of moisture in the gas, from the measured temperature.

32. The method of claim 31, further comprising the step of:
  (a) correcting regulation of the temperature of the resonant moisture-sensitive device in response to the measured temperature of the resonant moisture-sensitive device so as to substantially remove a temperature-dependent component from the condensation-dependent signal.

33. The method of claim 31, wherein the condensation-dependent signal indicates a change in frequency of the RF oscillator circuit.

34. The method of claim 31, wherein the condensation-dependent signal indicates a change in amplitude of the RF oscillator circuit.

35. The method of claim 31, wherein the condensation-dependent signal indicates a change in phase of the RF oscillator circuit.

36. The method of claim 31, wherein the condensation-dependent signal has an analog form, and further including the step of converting the condensation-dependent signal from analog form to digital form.

37. The method of claim 31, further including the steps of:
   (a) periodically elevating the temperature of the resonant moisture-sensitive device above the dewpoint; and
   (b) measuring the condensation-dependent signal at such elevated temperature to provide a reference level signal.

38. The method of claim 31, wherein the resonant moisture-sensitive device is a resonant surface acoustic wave device having a characteristic Q value.

39. The method of claim 38, wherein the Q value of the resonant surface acoustic wave device exceeds about 2,000.

40. The method of claim 31, wherein the resonant moisture-sensitive device has a high Q value.

41. The method of claim 40, wherein the Q value exceeds about 2,000.

42. The method of claim 31, wherein the output signal is the temperature of the resonant moisture-sensitive device at equilibrium.

43. A method for measuring humidity, comprising the steps of:
   (a) measuring a condensation-dependent signal output by an RF oscillator circuit including a resonant moisture-sensitive device having a surface that is essentially non-hygroscopic, sensitive to moisture in an ambient gas and subject to condensation of moisture from the gas onto the surface, the condensation-dependent signal being indicative of the amount of condensation on the surface of the resonant moisture-sensitive device;
   (b) monitoring the condensation-dependent signal of the RF oscillator circuit;
   (c) comparing changes in the condensation-dependent signal relative to a set point;
   (d) regulating the temperature of the resonant moisture-sensitive device in response to such changes so as to maintain the condensation-dependent signal nearly constant over time in the presence of time-varying moisture in the gas;
   (e) measuring the temperature of the resonant moisture-sensitive device; and
   (f) generating an output signal, indicative of the amount of moisture in the gas, from the measured temperature.

44. The method of claim 43, further comprising the step of:
   (a) correcting regulation of the temperature of the resonant moisture-sensitive device in response to the measured temperature of the resonant moisture-sensitive device so as to substantially remove a temperature-dependent component from the condensation-dependent signal.

45. The method of claim 43, wherein the condensation-dependent signal indicates a change in frequency of the RF oscillator circuit.

46. The method of claim 43, wherein the condensation-dependent signal indicates a change in amplitude of the RF oscillator circuit.

47. The method of claim 43, wherein the condensation-dependent signal indicates a change in phase of the RF oscillator circuit.

48. The method of claim 43, wherein the condensation-dependent signal has an analog form, and further including the step of converting the condensation-dependent signal from analog form to digital form.

49. The method of claim 43, further including the steps of:
   (a) periodically elevating the temperature of the resonant moisture-sensitive device above the dewpoint; and
   (b) measuring the condensation-dependent signal at such elevated temperature to provide a reference level signal.

50. The method of claim 43, wherein the resonant moisture-sensitive device is a resonant surface acoustic wave device having a characteristic Q value.

51. The method of claim 50, wherein the Q value of the resonant surface acoustic wave device exceeds about 2,000.

52. The method of claim 43, wherein the resonant moisture-sensitive device has a high Q value.

53. The method of claim 52, wherein the Q value exceeds about 2,000.

54. The method of claim 43, wherein the output signal is the temperature of the resonant moisture-sensitive device when the condensation-dependent signal is nearly constant.

* * * * *